United States Patent
Valenti

[11] Patent Number: 5,919,208
[45] Date of Patent: Jul. 6, 1999

[54] SUTURE BLOCK FOR SURGICAL SUTURES

[76] Inventor: Gabriele Valenti, Via Nicola Fabrizi, 8, Rome 00153, Italy

[21] Appl. No.: 09/031,513

[22] Filed: Feb. 27, 1998

Related U.S. Application Data

[63] Continuation-in-part of application No. PCT/IT97/00150, Jun. 25, 1997.

[30] Foreign Application Priority Data

Jun. 27, 1996 [IT] Italy ................... RM96A0451

[51] Int. Cl.⁶ .................................. A61B 17/04
[52] U.S. Cl. ............................................ 606/232
[58] Field of Search ................... 606/232, 157; 411/184–189, 511, 34–39, 43

[56] References Cited

U.S. PATENT DOCUMENTS

| | | |
|---|---|---|
| 2,075,508 | 3/1937 | Davidson. |
| 3,753,438 | 8/1973 | Wood et al.. |
| 3,976,079 | 8/1976 | Samuels et al.. |
| 5,258,015 | 11/1993 | Li et al.. |

FOREIGN PATENT DOCUMENTS

| | | |
|---|---|---|
| 0 012 360 | 6/1980 | European Pat. Off.. |
| 0 594 002 | 4/1994 | European Pat. Off.. |
| 0 634 142 | 1/1995 | European Pat. Off.. |
| 2 682 867 | 4/1993 | France. |
| WO 94/15535 | 7/1994 | WIPO. |

*Primary Examiner*—Michael Buiz
*Assistant Examiner*—Vikki Trinh
*Attorney, Agent, or Firm*—Browdy and Neimark

[57] ABSTRACT

A suture block is a device used to secure surgical sutures, without using knots. By securing the thread with a suture block, it is possible to close a suture in a contact with the tissue, without damaging or mortifying the latter, and without provoking icchemia in the tissue which is compressed by the loop of thread needed to tie a traditional surgical knot. This means that the surgeon no longer has to change the disposition of the operational field at each knot and can avoid having to put down the forceps or the needle-holder, in order to tie a normal knot, thereby saving time. Moreover, far less thread is required and most importantly, the pain caused by the knotted thread damaged and constricts the tissue, is significantly reduced.

10 Claims, 2 Drawing Sheets

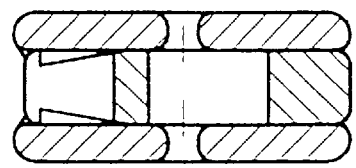
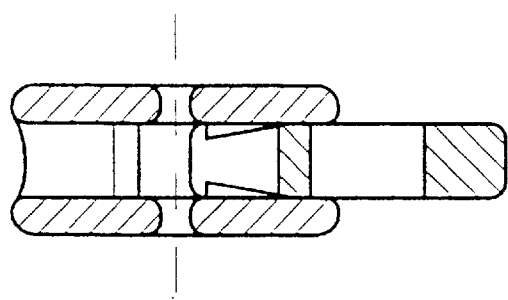
FIG. 2  FIG. 4
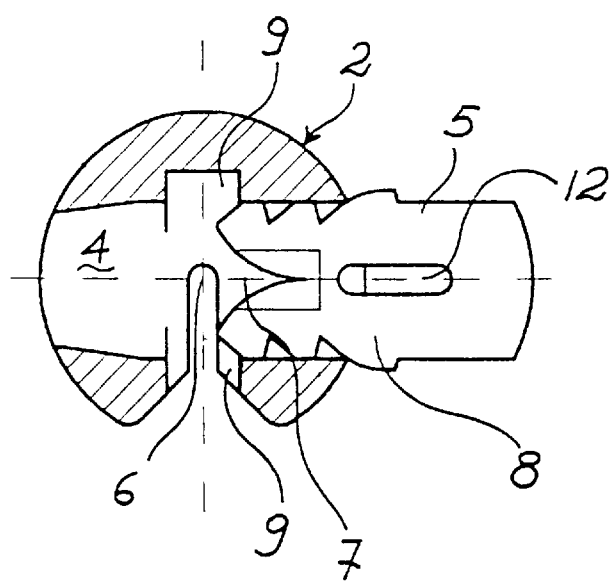
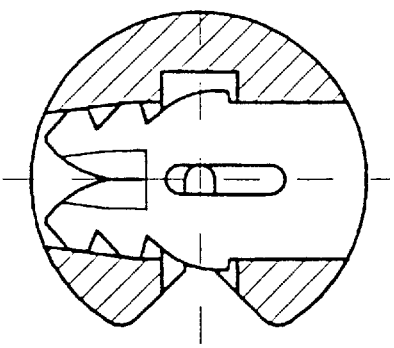
FIG. 1  FIG. 3

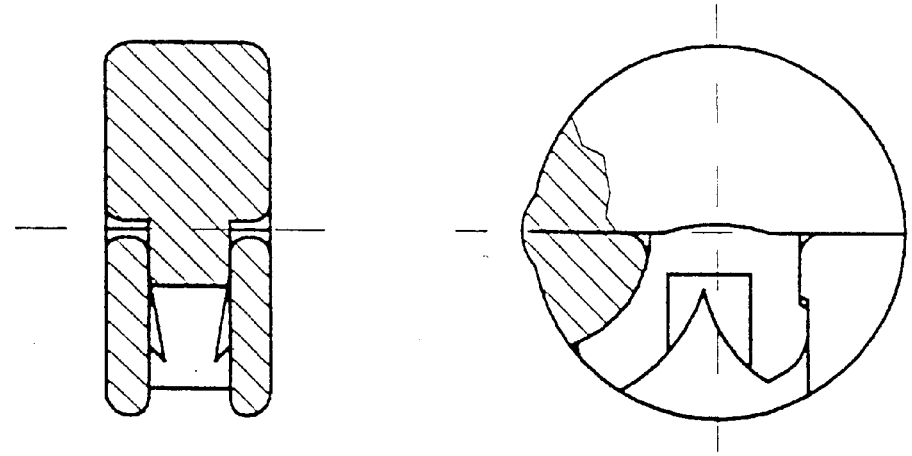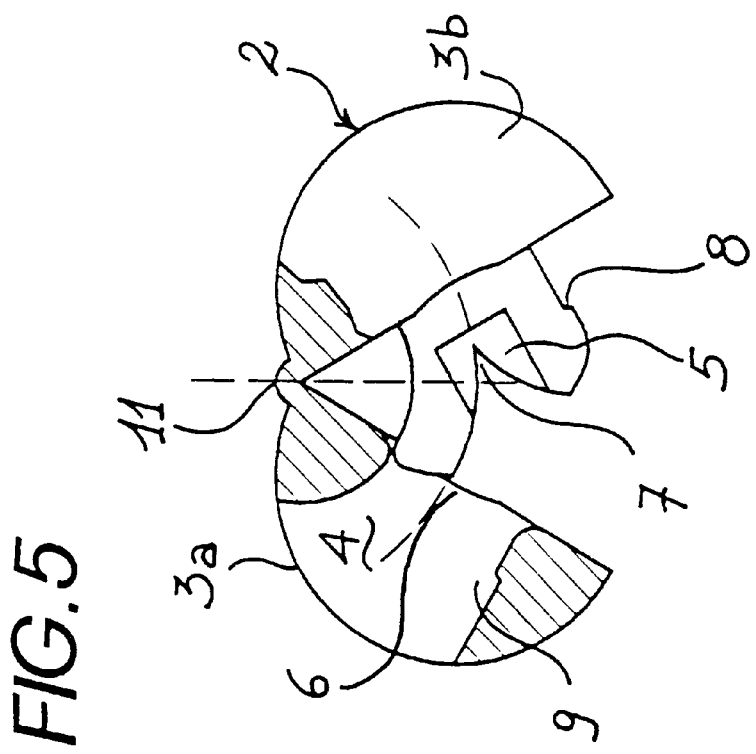

SUTURE BLOCK FOR SURGICAL SUTURES

CROSS REFERENCE TO RELATED APPLICATION

The present application is a continuation-in-part of PCT application No. PCT/IT97/00150, filed Jun. 25, 1997, which claims priority from Italian application No. RM96/A000451, filed Jun. 27, 1996, the entire contents of both of which are hereby incorporated by reference.

DESCRIPTION

A proposal for a suture block for surgical sutures. This carefully-devised invention is made of re-absorbable, non-re-absorbable, metallic or a blend of materials, just like normal two-part surgical sutures, which are joined together and secured to prevent the thread from coming undone. Apart form the traditional knot, the options which exist today as regards securing sutures, consist of metal clips or clips made of materials which are gradually reabsorbed. Clips, however, block the thread in the acute angle formed by the two linear parts before they are closed—in other words, in the vertex of the "V". Yet this an unsuitable and imbalanced position since the thread is subjected to traction and tension. Thus, instead of being and remaining in a perfectly orthogonal position in the direction of the traction, the clip tends to assume a vertical position, putting the tissue at one end under pressure and losing optimum surface contact—and hence much of the stability needed for it to serve its purpose. What's more, the linear form of the clip, once closed, is completely ineffectivetl in achieving the desired effect. Invented to hold vessels of tissue together, it is used incorrectly to secure threads. I should add that the use of metal clips entails the use of excessive amounts of material—something which the patent finds hard to accept and which, moreover, interferes with certain diagnostic techniques. Clips made of re-absorbable material do not grip the thread and pose the same problems in terms of stability and ergonomics.

Even the recent introduction of the Lapra-Ty suture block, which addresses the problem, does not entirely solve it. In practice, this invention works on the basis of the same principle as a normal clip, already outlined, combined with an eccentric clasp and stop, which thus give rise to its shortcomings, namely, its instability and poor ergonomics. The only difference is that it is thicker than a normal clip and thus relies on this increased contact surface area, in order to secure the thread. The manufacturers themselves suggest that it only be used with woven threads, i.e. with those which nay be compressed and flattened, and which have a limited diameter in other words, least resistant ones.

Another method of securing a thread is by passing it through a little bead followed by a small lead ring, which works like a cork and a lead pellet. This method which is used only for cutaneous sutures, has several drawbacks. Firstly, the surgeon is forced to thread the needle first through the bead and then through the lead pellet, which must finally be secured using a surgical instrument: secondly, there is the risk that the needle holder lose its grip, and having to chance instrument is a further waste of time. Besides, the threads available on the market are meant for continuous sutures and a similar procedure for sutures consisting of isolated stitches would be unthinkable, due to the sheer number of beads and lead pellets required, and the risk of confusion on the operating table, which could easily result. Lastly, the sphere which functions as a suture block and which is positioned between the tissue and the lead pellet, in theory only has punctiform contact with the tissue, when fill surface contact is what is really required. In fact, contact between the sphere and the tissue plane only occurs at the tangential point. The result here too is therefore also usatisfactory: in practice, the larger the contact surface area, the less is the pressure when equal force is applied, and, subsequently, the minor the damage done by the suture block to the tissue. The fact that none of these methods are used as a matter of course as a way to avoid tying knots, proves the point. In laparoscopic surgery the same problem exists—all the methods used to secure a suture are awkward and imprecise. Too many problems and risks are therefore involved, using clips for a different purpose from which they were intended, makes the surgeon feel uneasy, and the use of beads and lead pellets, is too complicated, empiric and haphazard. The innovations introduced with this invention are aimed at offering the surgeon with a new, quicker suture technique, which is less painfull and less traumatising for the tissue, and, on occasions, easier to perform.

The first characteristic of the invention is its disc-shaped form which provides the optimal surface area for contact with the tissue, whilst using the minimum of material. It thereby distributes the tension of the thread uniformly over the largest possible surface area.

The second characteristic of the invention is that it enables the thread to be passed through the centre of the disc thus saving time and, should there be traction, provides balance and stability, guaranteeing optimal, uniform contact between the surface of the disc and the tissue.

Another characteristic of the invention is its suture blocking system which prevents the thread from working itself loose and at the same time does not weaken it, which is fundamental given the tension to which it is regularly subjected.

Another characteristic of the invention is that it has a peg—the "male" part—which thanks to a labyrinthine system, gradually blocks the thread whatever its thickness (within, of course, the limits of the calibres and materials normally used in surgery).

Another characteristic of the invention is that it exploites the elasticity and plasticity of the materials normally used in surgery in order to obtain a suture block fashioned in such a way that as the peg gradually enters its female counterpart, the walls "give" because of their elastomeric properties, both in order to hold the thread in place and to adapt to its variable diameter, without compressing it to such an extent that its resistance is reduced.

Another characteristics of the invention is that the front face of the male peg has what could be described as a "V"-shaped mouth, which serves both to position the thread within the suture block, and to ensure that as the thread is introduced, it is gradually tightened, irrespective of its thickness, by a self-blocking system which is independent from the above-mentioned labyrinthine mechanism The self-blocking system is the result of the combined effect of the "V"-shaped mouth, and the light pressure to which the two jaws of the "V" are subjected as the suture stop is closed. It works in the same way as the sheet pins on a yacht.

Another characteristic of the invention is that the male part is locked into the shell by a press-stud, spring toggle, or a mixed system Another characteristic of the invention is that its shell may consist of two separate pieces, or may be a single system in which the parts are hinged together, or attached to each other by a film.

Another characteristic of the invention is that it has been designed in such a way as to ensure that the thread is always clamped at the centre of the system.

Another characteristic of the invention is that a suture which is bound to the tissue is obtained, without the latter being constricted by a knot. This lowers the risk of eschew reduces pain and limits tissue trauma and damage.

Another characteristic of the invention is that the edges are rounded and so they reduce the damage that could be caused should they come into contact with the tissue.

Another characteristic of the invention is the ease, simplicity and speed with which it may be applied, reducing the complexity, length and cost of the surgical operation.

Another characteristic of the invention is that once the disc has been secured at the end of a continuous or isolated—stitch suture by applying a second disc close to the previous one and then cutting the thread between the two, the suture can be made ready for the next stitch, with the suture block already in place at the end of the disc.

Another characteristic of the invention is that its saves on the large quantities of sutural thread normally required.

Another characteristic of the invention is that it can be applied independently, or with disposable loaders, as is the case with clips.

Another characteristic of the invention is to offer the surgeon the possibility of performing a suture involving several stitches, without having to change the disposition of the operational field and without having to put down his instruments to free his hands to tie the knots.

With reference to the Figures, the number 1 indicates a suture block for surgical sutures made of re-absorbable or non re-absorbable material. Specifically, the suture block 1 comprises a body 2 of essentially discoidal shape wherein it presents a through female cavity 4 obtained in at least one part 3a, 3b. The number 5 indicates a male peg which is destined to be stably coupled by forced insertion into the female cavity 4 through forced fastening means. Advantageously the peg 5 presents a Transverse through slot 12 which runs longitudinally to the length of the peg 5) to lighten and increase its elastic characteristics.

The discoidal body 2 presents centrally an opening 6 for the passage and the transverse positioning into said female cavity 4 of a suture thread. The opening 6 is destined to co-operate with a V-shaped opening 7, elastically deformable, presented by the front end of the male peg 5 centring and blocking the suture thread, whatever its thickness, through the forced insertion of the male peg 5 into said female cavity 4. As is seen in the drawing, the opening 6 may have the shape of a slot, the length and breadth of which are transverse to the insertion direction of the peg 5. As shown in FIGS. 1 and 5, the forced blocking means are constituted by at least one tooth 8 presented laterally by the male peg 5 snapping, at the end of the forced insertion, against at least one corresponding projection 9 presented by the inner surface of the female cavity 4. As shown in particular in FIGS. 1, 2, 3, 4, the female cavity 4 passes through the entire discoidal body 2. The opening 6 for the passage and the positioning of the suture thread is obtained orthogonally to said female cavity 4, from the periphery to the centre of the discoidal body 2. Also in the Figures it is shown that the male peg 5 is inserted from the outside of the discoidal body 2 by forced insertion into said female cavity 4 and it presents on both its sides multiple teeth 8 which are destined to snap against opposing projections 9 presented by the inner surface of the female cavity 4.

As shown in FIGS. 5, 6, 7 the discoidal body 2 comprises two semi-discoidal parts mutually connected at an end by a hinge element 11, wherein one of said semi-discoidal parts 3b presents integrally in correspondence with its inner surface the male peg 5 which is destined to be inserted by forced insertion into the female cavity 4 is obtained centrally in the other semi-discoidal part 3a by partial convergent rotation of said semi-discoidal parts 3a, 3b.

The opening 6 for the passage and positioning of the suture thread is obtained from opposite conforming central concavities obtained on the opposing inner surfaces of said two semi-discoidal parts 3a, 3b. Advantageously as shown in all figures the discoidal body 2 presents rounded peripheral edges.

Naturally, the present invention can be subject to numerous modifications and variations, without thereby departing from the inventive concept which characterises it.

I claim:

1. A suture block for holding a surgical suture thread, the block comprising:

a body (2), of essentially discoidal shape, including a through female cavity (4) in at least one part (3a, 3b) thereof;

a male peg (5) insertable into said female cavity (4) in an insertion direction and including a V-shaped opening at a front end thereof;

said discoidal body (2) including an opening (6) for passage and positioning, transverse to the insertion direction, of the suture thread into said female cavity (4), thereby to co-operate with the V-shaped opening (7) elastically deformable to center and block the suture thread, whatever its thickness, through a forced insertion of the male peg (5) and the thread into said female cavity (4) in the insertion direction;

said male peg (5) including at least one tooth (8) laterally fastening the peg by snapping at the end of the forced insertion against at least one corresponding projection (9) on an inner surface of the female cavity (4).

2. Suture block for surgical sutures, according to claim 1, wherein said female cavity (4) passes through the entire discoidal body (2) and wherein said opening (6) for the passage and the positioning of the suture thread is disposed orthogonally to said female cavity (4) and the insertion direction, from the periphery to the center of the discoidal body (2); said male peg (5) being inserted from the outside of the discoidal body (2) by the forced insertion into said female cavity (4) and including on both its sides multiple teeth (8) destined to snap against opposing projections (9) presented by the inner surface of the female cavity (4).

3. Suture block for surgical sutures, according to claim 2, characterised in that said male peg (5) includes a through slot (12) for lightening and for increasing the elastic characteristics of the male peg (5).

4. Suture block for surgical sutures, according to claim 1, characterised in that said discoidal body (2) comprises two semi-discoidal parts (3a, 3b) mutually connected at an end by a hinge element (11), wherein one of said semi-discoidal parts (3b) presents integrally in correspondence with its inner surface the male peg (5) destined to be inserted by forced insertion into the female cavity (4) obtained centrally in the other semi-discoidal part (3a) by partial convergent rotation of said semi-discoidal parts (3a, 3b).

5. Suture block for surgical sutures, according to claim 4, characterised in that said opening (6) for the passage and positioning of the suture thread is obtained from opposite conforming central concavities obtained on the opposing inner surfaces of said two semi-discoidal parts (3a, 3b).

6. Suture block for surgical sutures, according to claim 1, characterised in that the discoidal body (2) presents rounded peripheral edges.

7. Suture block for surgical sutures, according to claim 1, characterised in that it is manufactured in re-absorbable material.

8. Suture block for surgical sutures, according to claim 1, characterised in that it is manufactured in non re-absorbable material.

9. The suture block for surgical sutures according to claim 1, wherein the opening (6) comprises a transverse slot extending perpendicular to the insertion direction, and wherein the thread is carried out of the slot by insertion of the male peg (5).

10. The suture block for surgical sutures according to claim 9, wherein the thread is not pressed against a bottom end of the transverse slot by insertion of the male peg (5).

* * * * *